US00PP15072P2

(12) United States Plant Patent
Heims

(10) Patent No.: US PP15,072 P2
(45) Date of Patent: Aug. 3, 2004

(54) ***ATHYRIUM NIPONICUM* VAR. *PICTUM* PLANT NAMED 'BURGUNDY LACE'**

(50) Latin Name: *Athyrium niponicum var. pictum*
Varietal Denomination: Burgundy Lace

(75) Inventor: Daniel M. Heims, Portland, OR (US)

(73) Assignee: Terra Nova Nurseries, Inc., Tigard, OR (US)

( * ) Notice: Subject to any disclaimer, the term of this patent is extended or adjusted under 35 U.S.C. 154(b) by 19 days.

(21) Appl. No.: 10/421,335

(22) Filed: Apr. 22, 2003

(51) Int. Cl.[7] ..... A01H 5/00
(52) U.S. Cl. ..... Plt./379
(58) Field of Search ..... Plt./379

*Primary Examiner*—Bruce R. Campell
*Assistant Examiner*—Michelle Kizilkaya
(74) *Attorney, Agent, or Firm*—Klarquist Sparkman, LP

(57) ABSTRACT

A new and distinct hybrid of *Athyrium niponicum* var. *pictum* plant characterized by exceptional burgundy, pink, and silver colors of the fronds.

1 Drawing Sheet

Botanical name: *Athyrium niponicum* var. *pictum.*
Cultivar name: 'Burgundy Lace'.

The present invention relates to a new and distinct cultivar of *Athyrium niponicum* var. *pictum*, of the family Woodsiaceae, which originated as a chance sporling found by Dan Heims.

The new variety has been reproduced only by asexual propagation (division and tissue culture). Each of the clones exhibits identical characteristics to the original selection.

This plant is characterized by the deep burgundy tone to the leaves in addition to the silvering, giving the plant a unique pink appearance. This coloring is strongest on the new growth but persists better than any other clone on the market.

Asexual propagation by division and tissue culture as done in Canby, Oreg., shows that the foregoing characteristics and distinctions come true to type and are established and transmitted through succeeding propagations. The present invention has not been evaluated under all possible environmental conditions. The phenotype may vary with variations in environment without a change in the genotype of the plant.

BRIEF DESCRIPTION OF THE DRAWING

The drawing shows a two and a half year old *Athyrium niponicum* var. *pictum* 'Burgundy Lace' in a container in Canby, Oreg.

DETAILED PLANT DESCRIPTION

The following is a detailed description of the new *Athyrium niponicum* var. *pictum* selection based on observations of 2½ year old specimens grown in a gallon container in a cool greenhouse in Canby, Oreg. The color descriptions are all based on The Royal Horticultural Society Colour Chart.

Botanical name: *Athyrium niponicum* var. *pictum.*
Cultivar name: 'Burgundy Lace'.
Plant:
- *Form.*—Terrestrial, rhizomatous fern.
- *Hardiness.*—U.S.D.A. Zones 5 to 8.
- *Size.*—62 cm wide and 20 cm tall.

Stem: None above ground, rhizomatous. Rhizome is typical of *Athyrium nipponicum.*

Foliage:
- *Type.*—Compound.
- *Number of leaf blades.*—25.
- *Shape.*—Lanceolate. Twice pinnate. Pinnule is lanceolate to oblong.
- *Size.*—Grows to 30 cm long and 17 cm wide. Pinnules may be from 3 to 17 cm long and from 1 to 3 cm wide.
- *Margins.*—2 pinnate. Pinnule is lobed and incised.
- *Apex.*—Acuminate, pinnatifid.
- *Base.*—Rounded to truncate.
- *Venation.*—Pinnate.
- *Texture.*—Glabrous.
- *Rachis texture.*—Glabrous but with chaffy scales (Greyed Orange 167A), mainly along the base but occasional elsewhere.
- *Rachis length.*—18 cm.
- *Rachis color.*—Greyed Purple 186A.
- *Leaf color.*—Young leaves: Burgundy, Greyed Purple 187A. Mature leaves are burgundy colored along the center ⅓ (Greyed Purple 187A) changing to brown (Brown 200A) with silver sides for ⅔ of leaf (Greyed White 156C) with pink side veins (Red Purple 61A). Where leaves are brown the veins are burgundy (Greyed Purple 187A). Where silver and burgundy overlap the color is pink (Red 56B).

Fruiting body: Same as all *Athyrium niponicum* var. *pictum.*
- *Type.*—Sporangium.
- *Fertility.*—Fertile.
- *Sori.*—Shape — Covered with a superior confluent indusium, elongate, opening on one edge, the edge facing the end of the pinna. Location — Dorsal, on every pinnule, mostly on one side of the vein. Where on both sides it curls around to the other side near the tip.
- *Size.*—Varies with the pinnule size, usually 1 to 2 mm. long.
- *Immature.*—Greyed Orange 177A.
- *Sporulating.*—Brown 200D.

Disease: Have not observed any disease on plants grown commercially in Canby, Oreg.

DESCRIPTION OF PARENT PLANTS

The instant plant resulted from a selection of *Athyrium niponicum* var. *pictum. A. niponicum,* as described in A–Z Encyclopedia of Garden Plants by the American Horticultural Society (1996), is a "Deciduous fern with creeping red-brown rhizomes and 2- or 3-pinnate to pinnatifid, lance-shaped, silvery gray-green or mid-green fronds, to 14 in (35 cm) long, with red-purple midribs . . . Segments are lance-shaped to oblong or ovate, sometimes with notched or lobed margins . . . [var. *pictum*] has fronds with purplish red stalks and silver-gray segments, sometimes flushed purple-red." The instant plant differs from *A. niponicum* var. *pictum* and named clones thereof (known to the applicant), such as 'Ursula's Red' (unpatented), in being substantially more burgundy in color.

I claim:

1. A new and distinct selection of *Athyrium niponicum* var. *pictum* plant substantially as shown and described, characterized by exceptional burgundy, pink, and silver colors of the fronds.

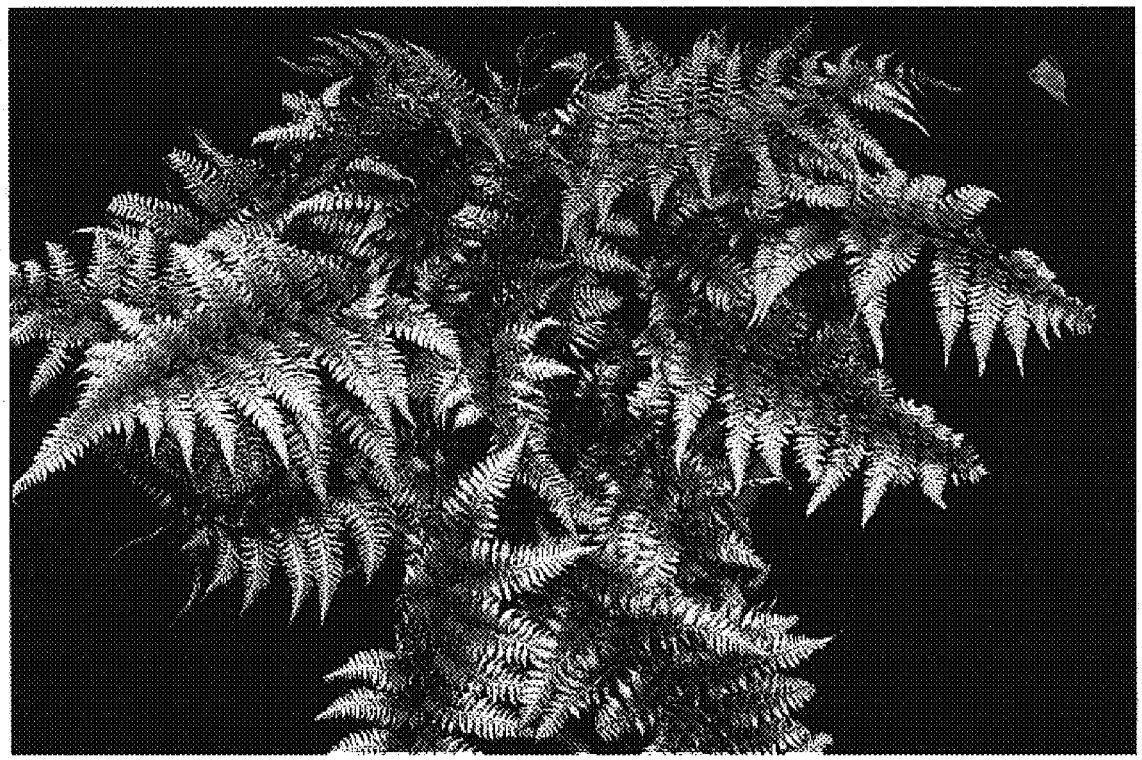

* * * * *